United States Patent
Dairiki et al.

(10) Patent No.: US 10,555,520 B2
(45) Date of Patent: Feb. 11, 2020

(54) PESTICIDE COMPOSITION POTENTIATED IN EFFICACY AND METHOD FOR POTENTIATING EFFICACY OF PESTICIDAL ACTIVE INGREDIENTS

(71) Applicant: Nippon Soda Co., Ltd., Chiyoda-ku, Tokyo (JP)

(72) Inventors: Hiroshi Dairiki, Odawara (JP); Rieko Nakamura, Odawara (JP)

(73) Assignee: Nippon Soda Co., Ltd., Tokyo (JP)

( * ) Notice: Subject to any disclaimer, the term of this patent is extended or adjusted under 35 U.S.C. 154(b) by 46 days.

(21) Appl. No.: 15/877,662

(22) Filed: Jan. 23, 2018

(65) Prior Publication Data

US 2018/0146664 A1    May 31, 2018

Related U.S. Application Data

(62) Division of application No. 12/675,192, filed as application No. PCT/JP2008/065101 on Aug. 25, 2008, now abandoned.

(30) Foreign Application Priority Data

Aug. 31, 2007   (JP) ................................. 2007-226839

(51) Int. Cl.
   *A01N 25/30*   (2006.01)
(52) U.S. Cl.
   CPC .................................... *A01N 25/30* (2013.01)
(58) Field of Classification Search
   CPC ........... A01N 25/30; A01N 25/04; C11D 1/72
   See application file for complete search history.

(56) References Cited

U.S. PATENT DOCUMENTS

| | | | |
|---|---|---|---|
| 5,187,191 A | 2/1993 | Otten et al. | |
| 5,500,219 A | 3/1996 | Utz et al. | |
| 5,846,905 A | 12/1998 | Frisch et al. | |
| 6,313,074 B1 | 11/2001 | Suzuki et al. | |
| 2002/0052406 A1 | 5/2002 | Sembo et al. | |

FOREIGN PATENT DOCUMENTS

| | | |
|---|---|---|
| DE | 10129855 A1 | 1/2003 |
| EA | 005860 B1 | 12/2003 |
| JP | 2004-292395 A | 10/2001 |
| JP | 2001-342102 A | 12/2001 |
| JP | 2004-098054 A | 4/2004 |
| RU | 2291619 C2 | 1/2005 |
| WO | WO 95/33379 A2 | 12/1995 |
| WO | WO 2005/084443 A1 | 9/2005 |
| WO | WO 2006/038631 A1 | 4/2006 |

OTHER PUBLICATIONS

Japanese Patent Office, International Search Report (translated) dated Sep. 16, 2008, from related International Patent Application No. PCT/JP2008/065101.
European Search Report dated Nov. 7, 2011, in EP 08828276.9, 6 pages.
Russian Office Action dated Feb. 3, 2011, in RU 2010106653, with English translation.
Office Action dated Mar. 13, 2012, in U.S. Appl. No. 12/675,192.
Office Action dated May 8, 2014, in U.S. Appl. No. 12/675,192.
Office Action dated Aug. 13, 2015, in U.S. Appl. No. 12/675,192.
Office Action dated Jul. 14, 2016, in U.S. Appl. No. 12/675,192.
Office Action dated Jul. 14, 2017, in U.S. Appl. No. 12/675,192.
Final Office Action dated Aug. 28, 2012, in U.S. Appl. No. 12/675,192.
Final Office Action dated Nov. 19, 2014, in U.S. Appl. No. 12/675,192.
Final Office Action dated Feb. 9, 2016, in U.S. Appl. No. 12/675,192.
Final Office Action dated Jan. 19, 2017, in U.S. Appl. No. 12/675,192.
Nippon Nyukazai Co., Ltd., "Nonionic Surfactant Newcol 2308 LY," Japanese product catalog, pp. 7-8, retrieved from http://nipponnyukazai.co.jp/file.jsp?id=306#page=4 on Apr. 26, 2016.
Nippon Nyukazai Co., Ltd., "Material Safety Data Sheet," Jan. 23, 2009.
CAS No. 70750-27-5, "C12-C13 ethoxylated propoxylated alcohols," from https://origin-scifinder.cas.org/scifinder/view/scifinder/scifinderExplore.jsf, (n.d.).
CAS No. 70750-27-5, "C12-C13 ethoxylated propoxylated alcohols," retrieved from http://www.chemicalbook.com/Search_JP.aspx?keyword=70750-27-5 on Apr. 26, 2016.
CAS No. 70750-27-5, "C12-C13 ethoxylated propoxylated alcohols," retrieved from http://www.lookchem.com/cas-707/70750-27-5.html, on Apr. 26, 2016.

*Primary Examiner* — Kyle A Purdy
(74) *Attorney, Agent, or Firm* — Foley & Lardner LLP

(57) ABSTRACT

The present invention provides a pesticide composition comprising a pesticidal active ingredient and a compound represented by chemical formula (I) or chemical formula (II)

R—O-(EO)$w$-(PO)$x$-(EO)$y$-(PO)$z$-H   (I)

R—O—(PO)$w$-(EO)$x$-(PO)$y$-(EO)$z$-H   (II)

(wherein, EO represents an ethyleneoxy group, PO represents a propyleneoxy group, R represents an alkyl or alkenyl group having 8 to 20 carbons, w represents on average an integer in the range of 1 to 25, x represents on average an integer in the range of 1 to 25, y represents on average an integer in the range of 1 to 25, and z represents on average an integer in the range of 1 to 25). Further the present invention provides a method for potentiating the efficacy of the pesticidal active ingredient comprising using a compound represented by chemical formula (I) or chemical formula (II) in combination with a pesticidal active ingredient.

4 Claims, No Drawings

PESTICIDE COMPOSITION POTENTIATED IN EFFICACY AND METHOD FOR POTENTIATING EFFICACY OF PESTICIDAL ACTIVE INGREDIENTS

CROSS-REFERENCE TO RELATED APPLICATIONS

This application is a Divisional of U.S. application Ser. No. 12/675,192, which is the U.S. National Stage application of PCT/JP2008/065101, filed Aug. 25, 2008, which claims priority from Japanese Application No. 2007-226839, filed Aug. 31, 2007.

TECHNICAL FIELD

The present invention relates to a pesticide composition containing a pesticide efficacy potentiating agent and a pesticidal active ingredient, and to a method for potentiating the efficacy of a pesticidal active ingredient.

Priority is claimed on Japanese Patent Application No. 2007-226839, filed Aug. 31, 2007, the content of which is incorporated herein by reference.

BACKGROUND ART

Numerous pesticide compositions, such as insecticides, fungicides, herbicides, miticides, plant growth regulators and the like, have long been employed. In order to fully draw out the effects of the pesticidal active ingredient, various trials have been carried out with respect to the type of formulation, i.e., emulsion, wattable powder, granules, powder, flowable agent, etc.

However, the method of fully drawing out the effects of the pesticidal active ingredient and enhancing the effects of the pesticide by manipulating the type of formulation has limitations.

A pesticide efficacy potentiating agent has therefore been proposed which, when used together with a pesticidal active ingredient, is capable of potentiating the efficacy of the pesticidal active ingredient.

For example, a pesticide efficacy potentiating agent is proposed in Patent Reference Document No. 1 which consists of a 3-dimensional copolymer having a (poly) ethyleneoxy group unit (EO), a (poly) propyleneoxy group unit (PO), and a (poly)ethyleneoxy group unit (EO) within the molecule.

However, while the pesticide efficacy potentiating agent disclosed in this reference is capable of potentiating the efficacy of the pesticidal active ingredient and thus decreasing the amount of pesticide employed, chemical damage sometimes depending on the use.

Patent Document 1: Japanese Unexamined Patent Application, First Publication No. H11-035406

DISCLOSURE OF THE INVENTION

Problems to be Solved by the Invention

The present invention was conceived in view of the above-described circumstances encountered in the conventional art, and has as its objective the provision of a pesticide composition which is capable of potentiating the efficacy of a pesticidal active ingredient without causing chemical damage, containing a pesticide efficacy potentiating agent and a pesticidal active ingredient. The present invention further relates to a method for potentiating the efficacy of a pesticidal active ingredient.

Means to Solve the Problems

The present inventors carried out exhaustive research to solve the problems disclosed above, and completed the present invention with the discovery that when using a pesticidal active ingredient, the efficacy of the pesticidal active ingredient can be potentiated without causing chemical damage by combined use of a compound having a specific polyoxyalkylene structure within the molecule.

The first embodiment of the present invention is a pesticide composition including a pesticidal active ingredient and a compound represented by chemical formula (I) or chemical formula (II)

[chemical formula 1]

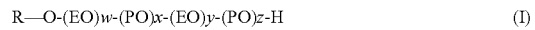

$$R\text{—}O\text{-}(EO)_w\text{-}(PO)_x\text{-}(EO)_y\text{-}(PO)_z\text{-}H \quad (I)$$

[chemical formula 2]

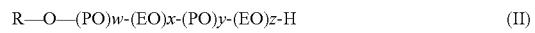

$$R\text{—}O\text{—}(PO)_w\text{-}(EO)_x\text{-}(PO)_y\text{-}(EO)_z\text{-}H \quad (II)$$

(wherein, in chemical formulas (I) and (II), EO represents an ethyleneoxy group, PO represents a propyleneoxy group, R represents an alkyl or alkenyl group having 8 to 20 carbons, w represents on average an integer in the range of 1 to 25, x represents on average an integer in the range of 1 to 25, y represents on average an integer in the range of 1 to 25, and z represents on average an integer in the range of 1 to 25.

The compound represented by chemical formula (I) or chemical formula (II) can be used as a pesticide efficacy potentiating agent which is capable of potentiating the efficacy of the pesticidal active ingredient.

The pesticide composition according to the present invention preferably includes a solvent and an adsorption carrier.

The pesticidal active ingredient of the pesticide composition according to the present invention is preferably a neonicotinoid type compound, and the neonicotinoid type compound is preferably an acetamiprid.

The second embodiment of the present invention is a method for potentiating the efficacy of the pesticidal active ingredient, comprising using a compound represented by chemical formula (I) or chemical formula (II) in combination with a pesticidal active ingredient.

Effects of the Invention

The pesticide composition according to the present invention employs a compound represented by chemical formula (I) or chemical formula (II) as the pesticide efficacy potentiating agent along with the pesticidal active ingredient to potentiate the efficacy of the pesticidal active ingredient. Further, the pesticide composition according to the present invention is highly stable and does not cause chemical damage or the like.

The method for potentiating the efficacy of the pesticidal active ingredient of the present invention enables potentiation of the efficacy of the pesticidal active ingredient which is employed. As a result, it is possible to reduce the amount of pesticidal active ingredient employed and to decrease chemical damage.

BEST MODE FOR CARRYING OUT THE INVENTION

The present invention will now be explained in detail.
1) Pesticide Efficacy Potentiating Agent The present invention includes a compound represented by chemical formula (I) (hereinafter referred to as "compound (I)"), or by the chemical formula (II) (hereinafter referred to as "compound (II)"). The present invention employs a compound represented by chemical formula (I) or chemical formula (II) as the pesticide efficacy potentiating agent.

Compound (I) and compound (II) are 4-dimensional copolymer having a (poly)ethyleneoxy group ($-C_2H_4-O-$) unit (EO), a (poly)propyleneoxy group ($-C_3H_6-O-$) unit (PO), a (poly)ethyleneoxy group ($-C_2H_4-O-$) unit (EO) and a (poly)propylene oxy group ($-C_3H_6-O-$) unit (PO) in the molecule.

In chemical formula (1), R represents an alkyl or alkenyl group having 8 to 20 carbons.

Examples of alkyl group having 8 to 20 carbons include straight or branched octyl, nonyl, decyl, undecyl, dodecyl and tridecyl groups or the like.

Examples of alkenyl group having 8 to 20 carbons include straight or branched octenyl, nonenyl, decenyl, undecenyl, dodecenyl and tridecenyl groups or the like.

w represents on average any integer in the range of 1 to 25, x represents on average any integer in the range of 1 to 25, y represents on average any integer in the range of 1 to 25, and z represents on average any integer in the range of 1 to 25. In the present invention, it is preferable that w, x, y and z each are in the range of 1 to 10 on average.

The polymer exists as a mixture of compounds having different number of unit. The term "average" here is the average value of the unit number.

Compounds (I) and (II) can be produced by a conventionally known method as disclosed in, for example, Japanese Patent Application, Publication No. 2004-98054. These compounds are also available commercially as Newcol 2308 LY and Newcol 2306HYT (both manufactured by Nippon Nyukazai Co., Ltd.), and may be used in this form without further modification.

2) Pesticidal Active Ingredient

The pesticidal active ingredient employed in the present invention is not particularly restricted, and an organic or inorganic compound may be used therefor. Further, a single compound or a mixture may be used. In addition, the form is not particularly restricted, with either liquid or solid forms acceptable.

Specifically, the fungicides, pesticides, miticides, herbicides, rodenticides, plant growth regulators, antibacterial agents, antifungal agents, anti-mold agents and the like shown below may be cited. These pesticidal active ingredients may be used alone or in combinations of two or more.

Examples of fungicides which may be cited include CNA, DPC, EDDP, IBP, PCNB, TPN, agrobacterium, isoprothiolane, ipconazole, iprodione, iminoctadine albesilate, iminoctadine acetate, imibenconazole, echlomezole, oxadixyl, oxycarboxin, oxytetracycline, oxine-copper, oxolinic acid, kasugamycin, carbendazole, quinoxaline, captan, chloroneb, diethofencarb, dicromezine, dithianon, zineb, difenoconazole, cyproconazole, dimethirimol, ziram, streptomycin, sulfenic acid-based (dichlofluanid), dazomet, thiadiazine, thiabendazole, thiophanate methyl, tiliadin, tecloftalam, tebuconazole, copper telephthalate, triadimefon, triazine, trichlamide, tricyclazole, triflumizole, triforine, triclofos methyl, copper nonylphenol sulfonate, validamycin, biter-tanol, hydroxyisoxazole, pyrazophos, pyrifenox, pyrooquilon, vinclozolin, fenarimol, ferimzone, fthalide, blasticidin, fluazinam, fluoroimide, flusulfamide, flutolanil, prochloraz, procymidone, propamocarb hydrochloride, propiconazole, propineb, probenazole, hexaconazole, pefurazoate, pencycuron, benthiazole, fosetyl, polyoxin, polycarbamate, myclobutanil, mildiomycin, methasulfocarb, metalaxyl, mepanipyrim, mepronil, copper sulfate probenazole, and the like.

Examples of insecticides which may be cited include BPMC, BPPS, BRP, CPCBS, CVMP, CVP, CYAP, DCIP, DEP, ECP, EPN, ESP, MIPC, MPMC, MPP, MTMC, PAP, PHC, PMP, XMC, acrinathrin, acetamiprid, acephate, amitraz, alanycarb, allethrin, isoxathion, isophenphos, imidacloprid, ethiofencarb, ethion, ethylthiometon, ethofenprox, ethoprophos MC, etrimfos, oxamyl, sodium oleate, cartap, carbosulfan, quinalphos, chlorfentezine, chlorpyrifos, chlorpyrifos-methyl, chlorfluazuron, chlorobenzilate, kelthane, salithion, dienochlor, cycloprothrin, cyhalothrin, cyfluthrin, diflubenzuron, cypermethrin, dimethylvinphos, dimethoate, cyromazine, sulprofos, diazinon, thiodicarb, thiometon, tetradifon, tebufenpyrad, tefluthrin, teflubenzuron, tralomethrin, nitenpyram, vamidothion, halfenprox, bifenthrin, pryaclofos, pyridaphenthion, pyridaben, pirimicarb, pyrimidifen, pirimiphos-methyl, fipronil, fenisobromolate, fenoxycarb, fenothiocarb, fenvalerate, fenpyroximate, fenpropathrin, buprofezin, furathiocarb, flucythrinate, prothiofos, propafos, profenofos, hexythiazox, permethrin, bensultap, benzoepin, benzomate, bendiocarb, benfuracarb, phosalone, fosthiazate, polynactin complex, polybutene, formothion, malathion, mesulfenfos, methomyl, metaldehyde, monocrotophos, resmethrin, levamysol hydrochloride, phenbutatin oxide, morantel tartrate, and the like.

Examples of miticides which may be cited include Smite (2-tert-butyl-5-(4-tert-butylbenzylthio)-4-chloropyridazin-3 (2H)-one), Acricid (2,4-dinitro-6-secondary-butylphenyl dimethylacrylate), Chlormit (isopropyl 4,4-dichlorobenzylate), Acar (ethyl-4,4-dichlorobenzylate), Kelthane [1,1-bis (p-chlorophenyl)-2,2,2-trichloroethanol], Citrazon (ethyl-O-benzoyl-3-chlor-2,6-dimethoxybenzohydroxymate), Omite [2-(p-tert-butylphenoxy)-cyclohexyl-2-propinyl sulfite], Osadan (hexakis(β,β-dimethylphenylethyl) distannoxane), Hexythiazox (trans-5-(4-chlorophenyl)-N-cyclohexyl-4-methyl-2-oxothiazolidine-3-carboxamide), Amitraz (3-methyl-1,5-bis(2,4-xylyl)-1,3,5-triazapenta-1,4-diene) and the like.

Examples of herbicides which may be cited include 2,4-PA, ACN, CNP, DAP, DBN, DCBN, DCMU, DCPA, DPA, DSMA, IPC, MBPMC, MCC, MCP, MCPB, MCPP, MDBA, PAC, SAP, TCA, TCTP, sethoxydim, ioxynil, asulam, atrazine, amiprophosmethyl, ametrine, alachlor, alloxydim, isouron, isoxaben, imazapyr, imazosulfuron, esprocarb, ethidimuron, oxadiazon, orthobencarb, karbutilate, quizalofop ethyl, quinclorac, glyphosate, chlormetoxinyl, clomeprop, chlorphthalim, cyanazine, sodium cyanate, diquat, dithiopyr, siduron, cinosulfuron, diphenamide, simazine, dimethametryn, simetryn, dimepiperate, terbacil, daimuron, thiazafluron, thifensulfuron-methyl, tetrapion, thenylchlor, tebuthiuron, triclopyr, trifluralin, naproanilide, napropamide, paraquat, bialaphos, picloram, bifenox, piperophos, pyrazoxyfen, pyrazosulfuron ethyl, pyrazolate, pyributycarb, fenoxaprop ethyl, phenothiol, phenmedipham, butachlor, butamifos, flazasulfuron, fluazifop, pretilachlor, prodiamine, propyzamide, bromacil, prometryn, bromobutide, hexadinone, bethrodine, bensulfuron methyl, benzophenap, bentazone, benthiocarb, pendimethalin, fosmaine ammonium, methyl daimuron, metsulfuron methyl, metolachlor, metribuzine, mefenaset, molinate, linuron, lenacil, and the like.

Examples of rodenticides which may be cited include coumarin derivatives, chlorophacinone, thallium sulfate, sodium monofluoroacetate, zinc phosphide and the like.

Examples of plant growth regulators which may be cited include abscisic acid, inabenfide, indole acetic acid, uniconazole, ethychlozate, ethephon, oxyethylene docosanol, oxine-sulfate, calcium chloride, calcium sulfate, calcium peroxide, quinoxaline, DEP, cloxyfonac, chlormequat, chlorella extract choline chloride, cyanamide, dichlorprop, gibberellin daminozide, decylalcohol, trinexapac-ethyl, paclobutrazol, paraffin, piperonyl butoxide, pyraflufenethyl, flurprimidol, prohydrojasmon, prohexadione-calcium, benzylaminopurine, pendimethalin, benfuracarb, inabenfide forchlorfenuron, potassium maleic hydrazide, mepiquat chloride, 1-naphthylacetamide, 4-CPA, MCPA thioethyl, MCPB and the like.

Examples of antibacterial agents, antifungal agents and anti-mold agents which may be cited include trialkyl triamine, ethanol, isopropyl alcohol, propyl alcohol, trisnitro, chlorobutanol, pronopol, glutaraldehyde, formaldehyde, α-bromocinnamaldehyde, Skane M-8, Kathon CG, NS-500W, BIT, n-butyl BIT, allyl isothiocyanate, thiabendazole, methyl 2-benzimidazolyl carbamate, lauricidin, BioBang, triclocarban, halocarban, glasisicar benzoic acid, sorbic acid, caprylic acid, propionic acid, 10-undecylenic acid, potassium sorbate, potassium propionate, potassium benzoate, monomagnesium phthalate, zinc undecylenate, 8-hydroxyquinoline, copper quinoline, TMTD, triclosan, dichlofluanilide, tolyfluanid, milt protein, egg white lysozyme, benthiazole, carbam-sodium triazine, tebiconazole, hinokitiol, tetrachloroisophthalonitrile, tectamer 38, chlorhexidine gluconate, chlorhexidine hydrochloride, polyhexamethylene biguanide, polybiguanide hydrochloride, danthoprom, clidant, sodium pyrithione, zinc pyrithione, densill, copper pyrithione, thymol, isopropyl methyl phenol, OPP, phenol, butyl barapen, ethyl paraben, methyl parapen, propyl parapen, metacresol, orthocresol, paracresol, sodium ortho-phenyl phenol, chlorophen, p-chlorophenol, parachloromethaxylate, parachlorocresol, fluor folpet, polylysine, Biopan P-1487, Jote methyl-paratolylsulfone, polyvinylpyrrolidone parachloroisocyanel, hydrogen peroxide, stabilized chlorine dioxide, peroxyacetic acid, copper naphthenate, Novalon AG300, silver chloride, titanium oxide, silver, zinc-calcium phosphate, Silver Ace, silver-zinc aluminosilicate, silver-zinc zeolite, Novalon AGZ330, Holon Killer, Dimer 136, benzalkonium chloride, didecyl dimethyl ammonium chloride, Bardac 2250/80, benzotonium chloride, Hyamine 3500J, cetyl ammonium bromide, cetrimide, CTAB, cetavlon, Dimer 38, benzalkonium chloride, Hyamine 3500J Bardac 170P, DC-5700, cetylpyridinium chloride, chitosan, diuron, DCMU, Prepentol A6, CMI, 2CI-OIT, BCM, ZPT, BNP, OIT, IPBC, TCMSP, and the like.

Neonicotinoid type compounds may be cited as preferred examples of the pesticidal active ingredient.

Specific examples of neonicotinoid type compounds include acetamiprid, imidacloprid, clothianidin, dinotefuran, thiacloprid, thiamethoxam, nitenpyram and the like.

The amount of the pesticidal active ingredient contained is not particularly restricted, but is typically in the range of 0.001 to 99 wt %, preferably in the range of 0.01 to 70 wt %, and more preferably in the range of 0.1 to 50 wt %, with respect to the pesticide composition in total.

Further, the proportion of the present invention's compound (I) or compound (II), and the pesticidal active ingredient that are used in the pesticide composition according to the present invention is not particularly restricted. However, as a weight ratio, it is preferable that: {compound (I) or compound (II)}/(pesticidal active ingredient)=0.03/1 to 50/1, more preferably 0.04/1 to 20/1, and even more preferably 0.1/1 to 10/1. When the amount of compound (I) or compound (II) employed with respect to the pesticidal active ingredient is in the above-referenced range, it is possible to relatively increase the potentiating effect on the efficacy of the pesticide which is desired, as compared to when these values are less than the above-cited ranges. On the other hand, even if the amount of compound (I) or compound (II) used with respect to the pesticidal active ingredient exceeds the above-cited range, the increase in efficacy beyond that cited above is not desirable.

3) Other Ingredients

It is preferable to include a solvent in the pesticide composition according to the present invention. As a result, a liquid pesticide composition having a superior potentiating effect on the efficacy of the pesticidal active ingredient and a reduced chemical damage can be obtained.

The employed solvent is not particularly restricted, so long as it is permitted from an agricultural and horticultural perspective. Examples which may be cited include water, alcohol-based solvents, ether-based solvents, phenol-based solvents, heterocyclic ring-based solvents, hydrocarbon-based solvents, ester-based solvents, amide-based solvents, ketone-based solvents, sulfur containing-based solvents, and mixed solvents of two or more of these.

Examples of alcohol-based solvents which may be cited include ethanol, n-propanol, isopropanol, n-butanol, neopentanol, n-hexanol, heptanol, n-octanol, isoctanol, 2-ethylhexanol, dodecyl alcohol, tridecyl alcohol, oleyl alcohol, ethylene glycol, diethylene glycol, glycerol, propylene glycol, dipropylene glycol, hexylene glycol, tetrahydrofurfuryl alcohol, glycerin, 1-thioglycerol, 3-methoxy-1-butanol, 2-mercaptoethanol, cyclohexanol, 3-methyl-3-methoxy-1-butanol, butyl diglycol, furfuryl alcohol, ethylene diglycol, ethyleneglycol diacetate, isopropylene glycol, 2-(2-chloroethoxy)ethanol, 1,3-butane diol, 2-ethyl-1-hexanol, 1,5-pentane diol, triethylene glycol, ethylene triglycol, 1,4-butane diol, 3-methyl-1,5-pentane diol, 2-methyl-2,4-pentane diol, polyethylene glycol, thiodiglycol, isoamyl alcohol, 5-dimethyl-1-hexyn-3-ol, nonyl alcohol, 3-chloro-1-propanol, decyl alcohol, ethylene glycol monoacetate, octane diol, 2-phenoxyethanol, 1,2,6-hexanetriol, polypropylene glycol, 1,3-butylene glycol methacrylate, ethylene glycol methacrylate, tetraethylene glycol methacrylate, triethylene glycol methacrylate, guecol, glycidol, cyclohexanol, 1-methylcyclohexanol, 2,4-xylenol, 3,5-xylenol, and the like.

Examples of ether-based solvents which may be cited include ethylene glycol monomethyl ether, ethylene glycol monoethyl ether, diethylene glycol dimethyl ether and the like.

Examples of phenol-based solvents which may be cited include cresol, octyl phenol, nonyl phenol, triisobutyl phenol, tristearyl phenol and the like.

Examples of heterocyclic ring-based solvents which may be cited include N-methyl-2-pyrrolidone, γ-butyrolactone, propylene carbonate and the like.

Examples of hydrocarbon-based solvents which may be cited include such aromatic hydrocarbons as benzene, toluene, xylene, mesitylene, ethylbenzene or the like; condensed aromatic hydrocarbons such as naphthalene, 1-methyl naphthalene, 2-methyl naphthalene, dimethyl naphthalene, indan, tetralin and the like; saturated or unsaturated cyclic aliphatic hydrocarbons such as cyclohexene, cyclohexin, cyclohexane, methylcyclopentane, and the like; and straight or branched, saturated or unsaturated aliphatic hydrocarbons such as pentane, hexane, octane, 2-methylbutane, 2,2,4-trimethyl pentane, and the like.

Examples of ester-based solvents which may be cited include such hydroxyl-carboxylic esters as formic acid ester, acetic acid ester, propionic acid ester, erucic acid ester, lauric acid ester, palmitic acid ester, stearic acid ester, oleic acid ester, linoleic acid ester, linolenic acid ester, and the like; such hydroxycarboxylic acid esters as lactic acid ester, citric acid ester and the like; such aliphatic polycarboxylic acid esters as oxalic acid ester, malonic acid ester, succinic acid ester, glutaric acid ester, adipic acid ester, pimelic acid ester, sebacic acid ester, azelaic acid ester, suberic acid ester, maleic acid ester, phthalic acid ester, terephthalic acid ester, mellitic acid ester, trimellitic acid ester, polymaleic acid ester and the like; such aromatic carboxylic acid esters as benzoic acid ester, phthalic acid ester and the like; among others.

As an example of these esters, alkyl ester having 1 to 10 carbons such as methyl ester, ethyl ester, n-propyl ester, isopropyl ester, n-butyl ester, isobutyl ester, s-butyl ester, t-butyl ester, n-pentyl ester, and isopentyl ester, among others, may be cited.

As an example of amide-based solvents, N,N-dimethyl formamide, N,N-dimethyl acetamide and the like may be cited.

As an example of ketone-based solvents, acetone, methylethylketone, cyclohexanone, isophorone, diacetone alcohol, methyl isobutyl ketone, methyl-n-amyl ketone, 2-methyl-2-pentene-4-one, acetophenon, and the like may be cited.

As examples of sulfur containing-based solvents, dimethyl sulfoxide (DMSO), sulfolane and the like may be cited.

As examples of animal and plant oil-based solvents, castor oil, coconut oil, palm oil, rapeseed oil, flaxseed oil, cottonseed oil, soybean oil, tung oil, squalane, sardine oil and the like may be cited.

The amount of solvent employed is not particularly restricted, but is typically in the range of 1 to 99.9 wt %, and preferably in the range of 30 to 96 wt %, with respect to the total pesticide composition.

It is preferable that an adsorption carrier be included in the pesticide composition according to the present invention. Even in the case of a solid pesticide composition containing an adsorption carrier, it is possible to obtain a superior efficacy potentiating effect on the pesticide active ingredient and reducing effect on chemical damage. Further, by including an adsorption carrier, it is possible to obtain a solid pesticide composition with excellent dilution properties. Namely, a pesticide composition can be obtained which, when diluting in water, has superior selfdispersibility, does not readily flocculate, has low foaming and a small amount of sedimentation.

The adsorption carrier employed is not particularly restricted as long as it is able to absorb compound (I) or compound (II). Examples which may be cited include amorphous silica (white carbon), diatomite, zeolite, Attapulgite, acid clay and the like Among these, amorphous silica and diatomite are preferred due to their high ability to absorb oil.

Specific examples of amorphous silica include Nipsil NS-K and Nipsil NS-KR manufactured by Tosoh Corp.; Carplex #80, Carplex #67 and Carplex #1120 manufactured by DSL. Japan Co., Ltd; Tokusil NSK and Tokusil P manufactured by Tokuyama Corp.; and AEROSIL 130, AEROSIL 200, AEROSIL 300, and AEROSIL 380 manufactured by Nippon Aerosil Co. Ltd.

Specific examples of diatomite include such dry diatomites as DiaFil 610 and DiaFil 615 manufactured by Celite Corporation, Radiolite S PF manufactured by Showa Chemical Industry Co., Ltd., Kunilite 201 manufactured by Kunimine Industries Co. Ltd., and oplite P-1300 manufactured by Oplite Mining Industry; such sintered diatomite manufactured products as Radiolite #100, Radiolite 200, Radiolite #500, Radiolite #800, and Radiolite Fine Flow B manufactured by Showa Chemical Industries Co., Ltd; and such flux-sintered diatomite manufactured products as Radiolite Microfine, Radiolite F, Radiolite Clear Flow, and Radiolite #2000 manufactured by Showa Chemical Industries Co., Ltd., and Zemlite 3Y manufactured by Hakusan Corp.; among others.

The amount of adsorption carrier employed is not particularly restricted, but is typically in the range of 1 to 99.9 wt %, preferably in the range of 20 to 80 wt %, and more preferably in the range of 30 to 70 wt %, with respect to the pesticide composition in total.

The pesticide composition according to the present invention may include a surfactant. By including a surfactant, it is possible to further improve the effect of potentiating the efficacy of the pesticidal active ingredient, and to decrease chemical damage.

The surfactant is not particularly restricted, and nonionic surfactants, anionic surfactants, cationic surfactants and amphoteric surfactants may be employed.

Examples of nonionic surfactants include polyoxyethylene alkyl ether, polyoxyalkylene alkyl ether, polyoxyethylene alkyl arlyl ether, polyoxyethylene stearyl phenyl ether, polyoxyethylene vegetable oil ether, polyoxyethylene aliphatic acid ester, polyoxyethylene sorbitan aliphatic acid ester, polyoxyethylene phenyl ether polymer, polyoxyethylene alkylene aryl phenyl ether, polyoxyalkylene aryl phenyl ether, polyoxyethylene alkylene glycol, and polyoxyethylene polyoxypropylene block polymer; fluorinated surfactants (perfluoroalkyl carboxylic acid, etc.); silicon-based surfactants (polyoxyalkylene dimethyl polysiloxane copolymer, etc.); acetylene glycol-based surfactants (2,4,7,9-tetramethyl-decyne-4,7-diol, etc.); and the like.

Examples of cationic surfactants include such alkyl amine ethylene oxide adducts as tallow amine ethylene oxide adduct, oleyl amine ethylene oxide adduct, soy amine ethylene oxide adduct, cocoamine ethylene oxide adduct, synthetic alkyl amine ethylene oxide adduct, and octyl amine ethylene oxide adduct; alkyl amine propylene oxide adduct; the alkanol amine alkyl esterified compound, alkylene oxide adducts thereof disclosed in pamphlet WO95/33379, and quaternary ammonium compound derived from these compounds; and mixtures thereof.

Examples of anionic surfactants include polycarboxylic acid surfactant, ligninsulfontate, alkylarylsulfonate, dialkyl sulfosuccinate, polyoxyethylene alkyl aryl ether sulfate, alkyl naphthalene sulfonate, polyoxyethylene stearyl phenyl ether sulfate, alklyl benzene sulfonate, alkyl sulfate, and the like.

Examples of amphoteric surfactants include lauryl dimethylamineoxide, Armox C/12, amineoxide, Monaterics, Miranols, betaine, Lonzaines, and mixtures thereof.

These surfactants may be used alone or in combinations of two or more.

Although the ratio of the compound (I) or compound (II) to the surfactant are not particularly restricted in the pesticide composition according to the present invention, with a weight ratio of {(compound (I) or compound (II)}/(other surfactant)=1/10 to 50/1 is preferred, and a weight ratio of {(compound (I) or compound (II)}/(other surfactant)=1/1 to 10/1 is even more preferred.

It is acceptable to formulate the pesticide composition according to the present invention by mixing in as desired a solvent or adsorption carrier, and/or a surfactant with compound (I) or compound (II), and the stirring the obtained mixture.

The compound (I) or compound (II) employed in the present invention is superior with respect to its effect on increasing the efficacy of the pesticidal active ingredient, and does not cause chemical damage. Accordingly, it is possible to reduce the amount of pesticidal active ingredient employed, or to decrease the amount of chemical damage with no change in the used amount of the pesticidal active ingredient.

Other components such as chelating agents, pH adjustors, inorganic salts, and viscosity enhancers may be included in the pesticide composition according to the present invention within a range which does not impair the effects of the present invention.

In the pesticide composition according to the present invention, additives may be added as needed to compound (I) or compound (II), the at least one type of pesticidal active ingredient, and, as desired, solvent or adsorption carrier, and/or surfactant, etc., and solid carriers, liquid carriers and gas carriers may be mixed in, or the pesticide composition may be impregnated into a porous ceramic plate or base agent such as a nonwoven cloth, so that the pesticide composition of the present invention may be formulated into the states used for conventional pesticides. Examples of pesticide states which may be cited include wattable powder, granular formulation, dust formulation, emulsion formulation, water-soluble chemicals, suspension agents, granular wattable powder, flowable, aerosol, smoke and misting agents, heat steam agents, fumigants, poison baits, microcapsules or the like.

Examples of the additives and carriers which may be employed in the case where a solid agent is desired include vegetable powders such as soybean or wheat flour; mineral micropowders such as diatom clay, apatite, plaster, talc, bentonite, pyrophyllite, clay and the like; and organic and inorganic compounds such as benzoate soda, urea, Glauber's salt, and the like.

Examples of the solvents which may be employed in the case where a liquid agent is desired include petroleum distallates such as kerosene, xylene and solvent naphtha, as well as cyclohexane, cyclohexanone, dimethylformamide, dimethylsulfoxide, alcohol, acetone, methylisobutylketone, mineral oil, vegetable oil, water and the like.

Examples which may be cited for a gas carrier employed in a spray agent include butane gas, LG, dimethyl ether and carbon dioxide gas.

The pesticide composition according to the present invention may be formulated by adding and stirring the compound (I) and compound (II) of the present invention into a formulated or commercially available pesticide composition or pesticide formulation which contains at least one type of pesticidal active ingredient.

As in the case of conventional pesticide compositions, the pesticide composition according to the present invention may be employed as is without modification, or may be diluted in water or the like, and used over seeds, plants, water surfaces or soil. Further, the pesticide composition according to the present invention may be used in combination with other fungicides, insecticides, herbicides, sreaders, fertilizers, soil improving agents and the like.

The pesticide composition according to the present invention may be used in the treatment of both agricultural and non-agricultural land.

In the case of agricultural land treatments, the pesticide composition according to the present invention may be employed as a seed treating agent in such treatments on seed potato as spraying, coating, spraying-coating, soaking, etc.; as a foliage treating agent in such treatments as spraying, top dressing, etc.; as a soil treating agent in such treatments as surface spraying, mixture treatment, irrigation treatment, fumigation, planting hole treatment, plant foot treatment, planting row treatment, infurrow treatment, nursery box treatment, nursery pot treatment, etc.; as a rice paddy treating agent in such treatments as giant forming tablets treatment, flowable agent treatment, etc.; and as a treating agent in such treatments as fumigation, lawn treatment.

In the case of non-agricultural land treatments, the pesticide composition according to the present invention may be employed as a soil pests and disease control agent, termite control agent, pest control agent, wood pest control agent, bait, animal external parasite control agent, health related pest control agent, household insecticide, algaecide for fishing nets and the like, anti-mildew agent for wood and the like, etc.

The applied amount of the pesticide composition according to the present invention which is employed will depend on the types of pesticidal active ingredient employed, climate conditions, formulation, application method, application site, target disease, target crop and the like. However, typically the quantity of effective component compound is 1 to 1000 g, and preferably 10 to 100 g per 1 hectare.

The efficacy of the pesticidal active ingredient are sufficiently displayed due to the action of the compound (I) or compound (II) included in the pesticide composition according to the present invention. For this reason, the pesticide composition according to the present invention has high pesticidal activity and low chemical damage as compared to a pesticide composition which does not include either compound (I) or compound (II).

4) Method for Potentiating Efficacy of Pesticidal Active Ingredient

The second invention is a method for potentiating the efficacy of the pesticidal active ingredient, characterized in employing the compound (I) or compound (II) according to the present invention as the pesticide efficacy potentiating agent when employing a pesticidal active ingredient.

More specifically, examples of methods for potentiating the efficacy of the pesticidal active ingredient according to the present invention include:

(a) a method of dispersing the pesticide composition according to the present invention;

(b) a method of mixing (tank mixing) together the compound (I) or the compound (II) of the present invention with a pesticide formulation that includes at least one type of pesticidal active ingredient at specific proportions, and then dispersing the obtained mixture; and (c) a method of dispersing a pesticide formulation containing the compound (I) or the compound (II) of the present invention and a pesticide formulation that includes at least one type of pesticidal active ingredient approximately simultaneously over the same target to be protected.

The present invention's method for potentiating the efficacy of a pesticidal active ingredient enables the efficacy of the pesticidal active ingredient employed to be increased. As a result, it is possible to decrease the amount of pesticidal active ingredient employed and to decrease the chemical damage.

EXAMPLES

Examples will now be cited to explain the present invention more specifically. However, the present invention is not limited in any way by the following examples.

Example 1

2.5 parts Newcol 2308LY (manufactured by Nippon Nyukazai Co., Ltd) employed as compound (I) or compound (II) (hereinafter referred to as "efficacy potentiating agent I"), dispersed per pot holding Japanese black pines (4 years old, pot cultivated). Once sufficiently dry, 10 pine branches were sampled from each pot. Then each pine branch was fixed inside a cup and one adult pine sawyer beetle was released therein. Accordingly, 10 cups (5 cups male, 5 cups female) were sampled per composition, and the effect of the insecticide was observed from Day 1 to Day 7. The observed results are shown in Table 1 below, as well as for the case of no treatment.

Note that in the table the maturation feeding area is the area of the new branch surface area of the pine which was eaten by one adult pine sawyer beetle.

"Withering" means the case where abnormal excitation such as spasm or the like are observed without causing death.

TABLE 1

Table 1

|  |  | Imago Quantity (insect number) | | | Death rate after 6 days | Maturation Feeding area after 7 days |
|---|---|---|---|---|---|---|
|  | Category | 1 day elapsed | 3 days elapsed | 6 days elapsed | elapsed (%) | elapsed ($cm^2$/insect) |
| Pesticide Composition 1 (Example 1) | Dead | 0 | 2 | 10 | 100% | 0.7 |
|  | Paralyzed | 4 | 4 | 0 |  |  |
|  | Normal | 6 | 4 | 0 |  |  |
| Pesticide Composition 2 (Example 2) | Dead | 0 | 2 | 10 | 100% | 0.5 |
|  | Paralyzed | 5 | 1 | 0 |  |  |
|  | Normal | 5 | 7 | 0 |  |  |
| Pesticide Composition 3 (Comp. Ex. 1) | Dead | 0 | 0 | 8 | 80% | 1.3 |
|  | Paralyzed | 2 | 2 | 2 |  |  |
|  | Normal | 8 | 8 | 0 |  |  |
| Untreated | Dead | 0 | 0 | 0 | 0% | 16.5 |
|  | Paralyzed | 0 | 0 | 0 |  |  |
|  | Normal | 10 | 10 | 10 |  |  |

2.2 parts acetamiprid employed as the pesticidal active ingredient, and 12.5 parts γ-butylolactone and 82.8 parts dipropylene glycol employed as the solvent were mixed and dissolved to obtain a uniform pesticide composition 1.

Example 2

2.5 parts of an efficacy potentiating agent I employed as the compound (I) or the compound (II), 2.2 parts acetamiprid employed as the pesticidal active ingredient, and 12.5 parts N-methyl-2-pyrrolidone and 82.8 parts dipropylene glycol employed as the solvent were mixed and dissolved to obtain a uniform pesticide composition 2.

Comparative Example 1

1 part metal salt of dioctyl sulfosuccinate (NK-EP-70G, 70%, manufactured by Takemoto Oil and Fat Co., Ltd.) employed as an efficacy potentiating agent, 2.2 parts acetamiprid employed as the pesticidal active ingredient, and 96.8 parts diethylene glycol employed as the solvent were mixed and dissolved to obtain a uniform pesticide composition 3.
(Test 1)
Tests on the efficacy of the pesticidal active ingredient on pine sawyer beetles were carried on for the pesticide compositions 1 to 3 obtained in Examples 1 and 2, and Comparative Example 1.
Each of the pesticide compositions 1 to 3 were diluted 200 fold with water, and 200 ml of the obtained solution was From Table 1, a superior insecticide effect was confirmed when employing pesticide compositions 1 and 2 as compared to when employing pesticide composition 3 or in the case of no treatment at all. Further, even in the case of withering, since the adult pine sawyer beetle cannot bite, the maturation feeding area is extremely reduced. Thus, the damage from the adult pine sawyer beetle could be greatly reduced.

Examples 3 to 5

Efficacy potentiating agent I, employed as compound (I) or compound (II), was added by stirring to each of the commercially available pesticide formulations aqueous Mospilan {4000 fold, manufactured by Nippon Soda Co., Ltd. (identical below)}, Nab emulsion {1000 fold, manufactured by Nippon Soda Co., Ltd. (identical below)}, and Topsin M wattable powder {(1000 fold, manufactured by Nippon Soda Co., Ltd. (identical below)}, to reach a concentration of 750 ppm, 500 ppm, and 250 ppm, respectively, thereby formulating pesticide compositions 4 to 6.

Comparative Examples 2 to 4

Pesticide compositions 7 to 9 were each formulated by adding Newcol 2303 (polyoxyethylene alkyl ether, manufactured by Nippon Nyukazai Co., Ltd., hereinafter referred to as "efficacy potentiating agent A") to aqueous Mospiran, Nab emulsion, and Topsin M wattable powder, respectively, to achieve concentrations of 750 ppm, 500 ppm, and 250 ppm.

Comparative Examples 5 to 7

Pesticide compositions 10 to 12 were each formulated by adding Newcol 2303Y (polyoxyethylene polyoxypropylene polyoxyethylene alkyl ether, manufactured by Nippon Nyukazai Co., Ltd., hereinafter referred to as "efficacy potentiating agent B") to aqueous Mospiran, Nab emulsion, and Topsin M wattable powder, respectively, to achieve concentrations of 750 ppm, 500 ppm, and 250 ppm.

(Test 2)

A specific quantity of the pesticide compositions 4 to 6 of Examples 3 to 5, the pesticide compositions 7 to 9 of Comparative Examples 2 to 4, and the pesticide compositions 10 to 12 of Comparative Examples 5 to 7 were each added to kidney bean leaves, and the presence of any chemical damage was detected. The results are shown in Table 2.

Note that in the table, the chemical damage index is a 0 to 10, ten-stage scale in which the value of the index increases as the degree of chemical damage worsens, i.e., where "0" is employed for the case where the leaves are observed to be completely healthy without any chemical damage detected, and "10" is employed for the case of death due to chemical damage.

Japan Co., Ltd.) in the amount of 7 parts was employed as the adsorption carrier, to obtain 14 parts absorbed product (1) in which the efficacy potentiating agent I is absorbed by the adsorption carrier. The obtained 14 parts adsorption product (1) was mixed in 10 parts Topsin M wattable powder and 76 parts Crown Clay in a coffee mill to obtain a uniform pesticide composition 13.

Comparative Example 8

An adsorption product (2) in the amount of 14 parts, in which 7 parts efficacy potentiating agent A is absorbed to 7 parts non-crystalline silica (Carplex #1120, manufactured by DSL. Japan Co., Ltd.), was mixed in a coffee mill with 10 parts Topsin M wattable powder and 76 parts Crown Clay to obtain a uniform pesticide composition 14.

Comparative Example 9

An adsorption product (3) in the amount of 14 parts, in which 50 parts efficacy potentiating agent B is absorbed to 50 parts non-crystalline silica (Carplex #1120, manufactured by DSL. Japan Co., Ltd.), was mixed in a coffee mill with 10 parts Topsin M wattable powder and 76 parts Crown Clay to obtain a uniform pesticide composition 15.

TABLE 2

Table 2

| | Pesticidal active ingredient | Pesticide Efficacy Potentiating Agent | | Concentration 250 ppm | 500 ppm | 750 ppm |
|---|---|---|---|---|---|---|
| Pesticide Composition 4 (Example 3) | aqueous Mospiran | Efficacy Potentiating Agent I | Chemical damage Index | 0 | 0 | 0.5 |
| Pesticide Composition 7 (Comp. Ex. 2) | | Efficacy Potentiating Agent A | | 1 | 4 | 6 |
| Pesticide Composition 10 (Comp. Ex. 5) | | Efficacy Potentiating Agent B | | 1 | 4 | 6 |
| Pesticide Composition 5 (Example 4) | NAB emulsion | Efficacy Potentiating Agent I | | 0 | 1 | 2 |
| Pesticide Composition 8 (Comp. Ex. 3) | | Efficacy Potentiating Agent A | | 1 | 4 | 5 |
| Pesticide Composition 11 (Comp. Ex. 6) | | Efficacy Potentiating Agent B | | 0.5 | 2 | 4 |
| Pesticide Composition 6 (Example 5) | Topsin M wattable powder | Efficacy Potentiating Agent I | | 0.5 | 1 | 2 |
| Pesticide Composition 9 (Comp. Ex. 4) | | Efficacy Potentiating Agent A | | 2 | 4 | 6 |
| Pesticide Composition 12 (Comp. Ex. 7) | | Efficacy Potentiating Agent B | | 2 | 4 | 4 |

From Table 2 it may be understood that in all cases pesticide compositions 4 to 6 which employ efficacy potentiating agent I had greatly reduced chemical damage as compared to pesticide compositions 7 to 12 which employ efficacy potentiating agent A or B.

Example 6

Efficacy potentiating agent I in the amount of 7 parts was employed as compound (I) or compound (II), and non-crystalline silica (Carplex #1120, manufactured by DSL.

(Test 3)

The pesticide compositions 13 to 15 obtained in Example 6 and Comparative Examples 8 and 9 were examined for self dispersibility when put into water, and foam height, amount of sedimentation and the presence of flocculation 30 minutes after inverting 30 times, and the dilution properties were tested.

Self dispersibility was evaluated with a visual inspection of the condition following introduction of the pesticide composition to a 100 ml Nessler tube into which 100 mL of 3 degree hard water had been introduced. The case where the pesticide composition settled with gradual deformation from the center of the Nessler tube was awarded a "O", while the case where the pesticide composition settled without deformation at all was awarded a "X".

The results of this evaluation are shown in Table 3 below.

The presence of flocculation was made after the evaluation of self dispersibility, by inverting the Nessler tube 30 times and performing the evaluation 30 minutes later. When flocculation of 1 mm or more in size was observed, a "+" was assigned, while the absence of flocculation was assigned as "−". The results of the evaluation are shown in Table 3 below. Foam height (mm) and sedimentation (mL) quantity were measured when evaluating for the presence of flocculation. The results of these measurements are shown in Table 3 below.

TABLE 3

|  | Pesticide Composition 13 (Example 6) | Pesticide Composition 14 (Comp. Ex. 8) | Pesticide Composition 15 (Comp. Ex. 9) |
| --- | --- | --- | --- |
| Self dispersibility | O | X | O |
| Presence of flocculation | − | + | − |
| Foam height (mm) | 0 | 4 | 17 |
| Amount of sedimentation (mL) | 0.1 | 0.5 | 0.1 |

Pesticide composition 13 has superior self dispersibility, and, even 30 minutes after dilution, does not flocculate, has no foam height and a low amount of sedimentation. In contrast, pesticide composition 14 has poor self dispersibility, and flocculates with a large amount of sedimentation 30 minutes after dilution. Pesticide composition 15 has excellent self dispersibility, with no flocculation and little sedimentation 30 minutes after dilution, but the foam height is great.

INDUSTRIAL APPLICABILITY

The present invention provides a pesticide composition having a highly effecatious pesticidal active ingredient and high stability, without chemical damage. Further, as a result of the present invention's method for potentiating the efficacy of the pesticidal active ingredient, it is possible to reduce the amount of pesticidal active ingredient employed and decrease the chemical damage, which has industrial benefits.

The invention claimed is:

1. A method for potentiating the efficacy of acetamiprid, comprising
preparing a composition consisting of a compound represented by formula (I), an acetamiprid, and a solvent: and dispersing the composition,
formula (I) having the following structure:

$$R\text{—}O\text{-}(EO)w\text{-}(PO)x\text{-}(EO)y\text{-}(PO)z\text{-}H \quad (I)$$

wherein, EO represents an ethyleneoxy group, PO represents a propyleneoxy group, R represents a dodecyl group or tridecyl group, w represents on average an integer in the range of 1 to 25, x represents on average an integer in the range of 1 to 25, y represents on average an integer in the range of 1 to 25, and z represents on average an integer in the range of 1 to 25*
wherein a ratio of the compound represented by formula (I) to the acetamiprid is 15/1 to 10/1, and
wherein a hydrophilic-lipophilic balance of the compound represented by formula (I) is 12.3.

2. The method according to claim 1, wherein an amount of the solvent is 1 to 99.9 wt % with respect to the total pesticide composition.

3. The method according to claim 1, wherein an amount of the acetamiprid is 0.1 to 50 wt % with respect to the total pesticide composition.

4. A method for potentiating the efficacy of acetamiprid, comprising
mixing a compound represented by formula (I), acetamiprid, and a surfactant other than the compound represented by chemical formula (I):

$$R\text{—}O\text{-}(EO)w\text{-}(PO)x\text{-}(EO)y\text{-}(PO)z\text{-}H$$

wherein EO represents an ethyleneoxy group, PO represents a propyleneoxy group, R represents a dodecyl group or tridecyl group, w represents on average an integer in the range of 1 to 25, x represents on average an integer in the range of 1 to 25, y represents on average an integer in the range of 1 to 25, and z represents on average an integer in the range of 1 to 25,
wherein the ratio of the compound represented by formula (I) to the acetamiprid is 15/1 to 10/1,
wherein the ratio of the compound represented by formula (I) to the surfactant is 1/10 to 50/1,
wherein the surfactant is at least one selected from the group consisting of a nonionic surfactant, an anionic surfactant, a cationic surfactant and an amphoteric surfactant, and
wherein a hydrophilic-lipophilic balance of the compound represented by formula (I) is 12.3.

* * * * *